United States Patent
Yedur et al.

(10) Patent No.: US 6,437,329 B1
(45) Date of Patent: Aug. 20, 2002

(54) USE OF CARBON NANOTUBES AS CHEMICAL SENSORS BY INCORPORATION OF FLUORESCENT MOLECULES WITHIN THE TUBE

(75) Inventors: Sanjay K. Yedur, Santa Clara; Bhanwar Singh, Morgan Hill; Bryan K. Choo, Mountain View, all of CA (US)

(73) Assignee: Advanced Micro Devices, Inc., Sunnyvale, CA (US)

( * ) Notice: Subject to any disclaimer, the term of this patent is extended or adjusted under 35 U.S.C. 154(b) by 0 days.

(21) Appl. No.: 09/428,098

(22) Filed: Oct. 27, 1999

(51) Int. Cl.$^7$ .......................... G21K 7/00; G01N 21/00; H01J 5/16
(52) U.S. Cl. .......................... 250/306; 356/73; 356/301; 250/234; 250/252
(58) Field of Search ................................ 250/306, 234, 250/252, 440.11; 356/73, 301

(56) References Cited

U.S. PATENT DOCUMENTS

| | | |
|---|---|---|
| 5,201,992 A | 4/1993 | Marcus et al. |
| 5,346,683 A | 9/1994 | Green et al. |
| 5,393,647 A | 2/1995 | Neukermans et al. |
| 5,424,054 A | 6/1995 | Bethune et al. |
| 5,457,343 A | 10/1995 | Ajayan et al. |
| 5,611,942 A | 3/1997 | Mitsui et al. |
| 5,747,120 A | 5/1998 | McLean, II et al. |
| 5,763,768 A | 6/1998 | Henderson et al. ............ 73/105 |
| 5,866,434 A | 2/1999 | Massey et al. |
| 5,877,412 A | 3/1999 | Muramatsu et al. |
| 5,916,642 A | 6/1999 | Chang |
| 5,986,256 A | * 11/1999 | Yagi ........................... 250/234 |
| 6,002,471 A | * 12/1999 | Quake ........................ 356/73 |
| 6,159,742 A | 12/2000 | Lieber et al. ............... 436/164 |

OTHER PUBLICATIONS

"Scanning Tunneling Microscope Update 1997", taken from the Internet at http://www.umsl.edu/~fraundor/stm97x.html, Oct. 21, 1999, 5 pages.
"Carbon Nanotubes and Related Structures", A carbon nanotube page, taken from the Internet at http://www.rdg.ac.uk/~scsharip/tubes.htm, Apr. 17, 2000, 6 pages.
"What is an Atomic Force Microscope?", taken from the Internet at http://www.che.utoledo.edu/nadarajah/webpages/whatsafm.html, Oct. 20, 1999, 2 pages.
"The Atomic Force Microscope (AFM)", taken from the Internet at http://www.sst.ph.ic.ac.uk/photonics/intro/AFM.html, Oct. 20, 1999, 2 pages.

* cited by examiner

Primary Examiner—Jack Berman
Assistant Examiner—K Fernandez
(74) Attorney, Agent, or Firm—Eschweiler & Associates, LLC

(57) ABSTRACT

A system for analyzing a film and detecting a defect associated therewith includes a scanning probe microscope having a nanotube tip with a material associated therewith which exhibits a characteristic that varies with respect to a film composition at a location corresponding to the nanotube tip. The system also includes a detection system for detecting the material characteristic and a controller operatively coupled to the detection system and the scanning probe microscope. The controller configured to receive information associated with the detected characteristic and use the information to determine whether the film contains a defect at the location corresponding to the nanotube tip. The invention also includes a method of detecting a film composition at a particular location of a film or substrate. The method includes associating a material exhibiting a characteristic which varies with respect to a film composition with a nanotube tip of a scanning probe microscope and detecting the characteristic. The method then includes the step of determining a composition of a portion of the film using the detected characteristic.

22 Claims, 5 Drawing Sheets

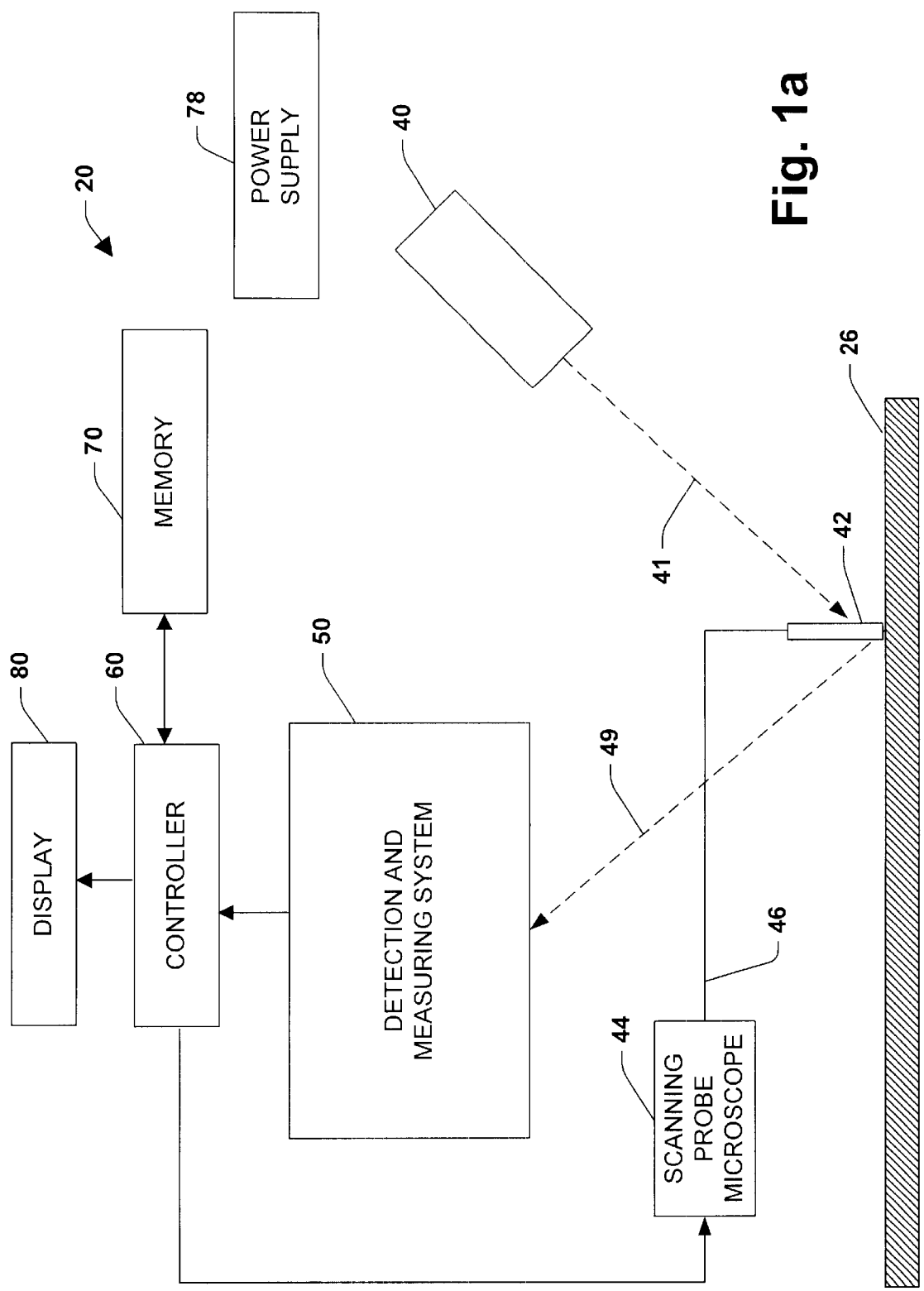

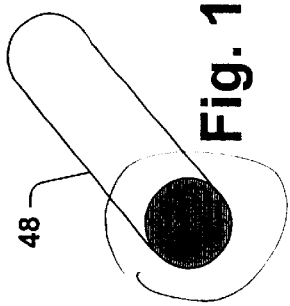
Fig. 1b
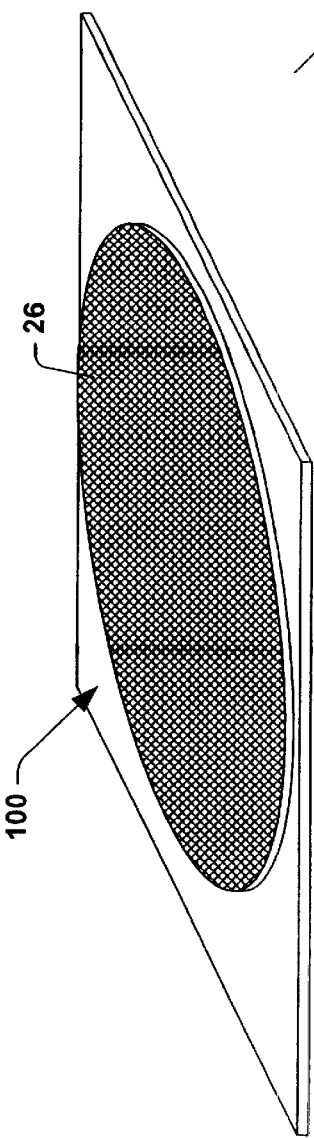
Fig. 2
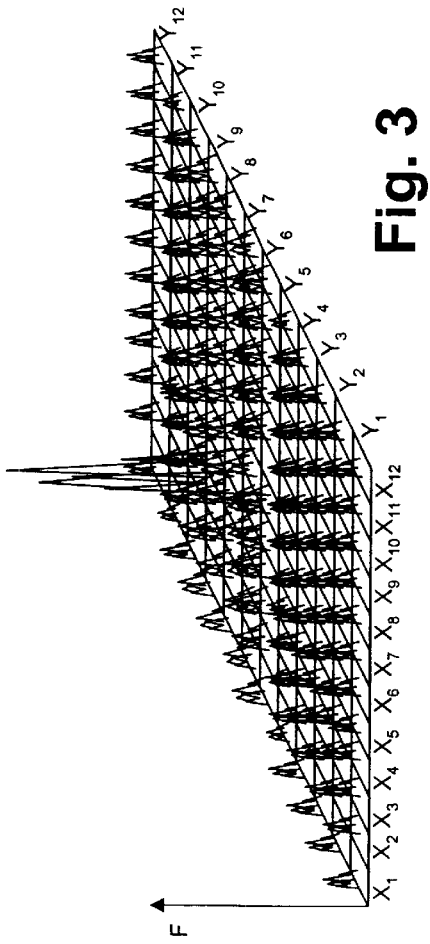
Fig. 3
Fig. 4

FILM ANALYSIS COMPLETE — 80

DEFECTS DETECTED : 1

DEFECT LOCATION(S): Xi, Yj

DEFECT ID: ALUMINUM

Fig. 6

USE OF CARBON NANOTUBES AS CHEMICAL SENSORS BY INCORPORATION OF FLUORESCENT MOLECULES WITHIN THE TUBE

TECHNICAL FIELD

The present invention generally relates to semiconductor processing, and in particular to a system and method for detecting defects on or in various films employed in semiconductor processing.

BACKGROUND OF THE INVENTION

In the semiconductor industry, there is a continuing trend toward higher device densities. To achieve these high densities there has been and continues to be efforts toward scaling down the device dimensions (e.g., at submicron levels) on semiconductor wafers. In order to accomplish such high device packing density, smaller and smaller features sizes are required. This may include the width and spacing of interconnecting lines, spacing and diameter of contact holes, and the surface geometry such as corners and edges of various features.

The requirement of small features with close spacing between adjacent features requires high resolution photolithographic processes. In general, lithography refers to processes for pattern transfer between various media. It is a technique used for integrated circuit fabrication in which a silicon slice, the wafer, is coated uniformly with a radiation-sensitive film, the resist, and an exposing source (such as optical light, x-rays, etc.) illuminates selected areas of the surface through an intervening master template, the mask, for a particular pattern. The lithographic coating is generally a radiation-sensitive coating suitable for receiving a projected image of the subject pattern. Once the image is projected, it is indelibly formed in the coating. The projected image may be either a negative or a positive image of the subject pattern. Exposure of the coating through a photomask causes the image area to become either more or less soluble (depending on the coating) in a particular solvent developer. The more soluble areas are removed in the developing process to leave the pattern image in the coating as less soluble polymer.

Due to the extremely fine patterns which are exposed on the photoresist, defect reduction becomes critical. Furthermore, as the patterns continue to decrease in size, the defect size of interest also decreases. That is, when feature sizes were large, the size of defects in a particular film had to exceed a minimum threshold to be of concern to the process designer. Now, however, the value of the minimum defect size threshold has substantially deceased, and the design of systems and methods for detecting such small defects has become extremely difficult.

It is therefore desirable to have a system and/or method which is capable of effectively and reliably detecting defects in various films employed in semiconductor manufacturing.

SUMMARY OF THE INVENTION

The present invention is directed toward a system and method of detecting a film or substrate composition or a defect within a known film or substrate using a scanning probe microscope employing a nanotube tip.

According to one aspect of the present invention, a scanning probe microscope is used to scan a film or substrate of interest. The scanning probe microscope employs a unique scanning tip formed of a nanotube such as a carbon nanotube. The carbon nanotube has a material encapsulated therein or coated thereon which exhibits a characteristic based on the film or substrate composition being scanned at the scanning tip. By monitoring the tip during the scanning process, the composition of the film or substrate may be identified as well as any defects located therein.

According to another aspect of the present invention, a carbon nanotube scanning probe microscope tip has a material which exhibits a fluorescence (e.g., a fluorophore) based on the composition of the film or substrate being scanned. For example, a light source such as a laser is focused on the carbon nanotube tip during scanning to excite the material therein. The fluorescence which emanates therefrom is a function of the film or substrate composition under the tip. For example, the fluorescence intensity or wavelength is detected and used as a signature to identify the film or substrate composition. By scanning the tip across the film or substrate sample, a defect or composition profile may be readily ascertained by evaluating changes in the tip fluorescence.

To the accomplishment of the foregoing and related ends, the invention, then, comprises the features hereinafter fully described and particularly pointed out in the claims. The following description and the annexed drawings set forth in detail certain illustrative embodiments of the invention. These embodiments are indicative, however, of but a few of the various ways in which the principles of the invention may be employed. Other objects, advantages and novel features of the invention will become apparent from the following detailed description of the invention when considered in conjunction with the drawings.

BRIEF DESCRIPTION OF THE DRAWINGS

FIG. 1a is schematic block diagram of a scanning probe system using a nanotube tip for detecting a film/substrate composition or defect associated therewith in accordance with the present invention;

FIG. 1b is a perspective view of an exemplary nanotube having a material encapsulated therein or coated thereon, wherein the nanotube is used as the scanning tip in the scanning probe microscope in accordance with the present invention;

FIG. 2 is a perspective illustration of a film/substrate, wherein the film/substrate has been mapped with a grid in accordance with the present invention;

FIG. 3 is a representative three-dimensional grid map of a film/substrate illustrating fluorescence amplitudes taken at grid blocks of the grid map in accordance with the present invention;

FIG. 4 is a fluorescence amplitude table correlating the fluorescence amplitudes of FIG. 3 with desired or expected values for the fluorescence amplitudes in accordance with the present invention;

FIG. 6 is a schematic diagram illustrating an exemplary display output providing defect detection information to a user in accordance with the present invention.

DETAILED DESCRIPTION OF THE INVENTION

Figure 1C:
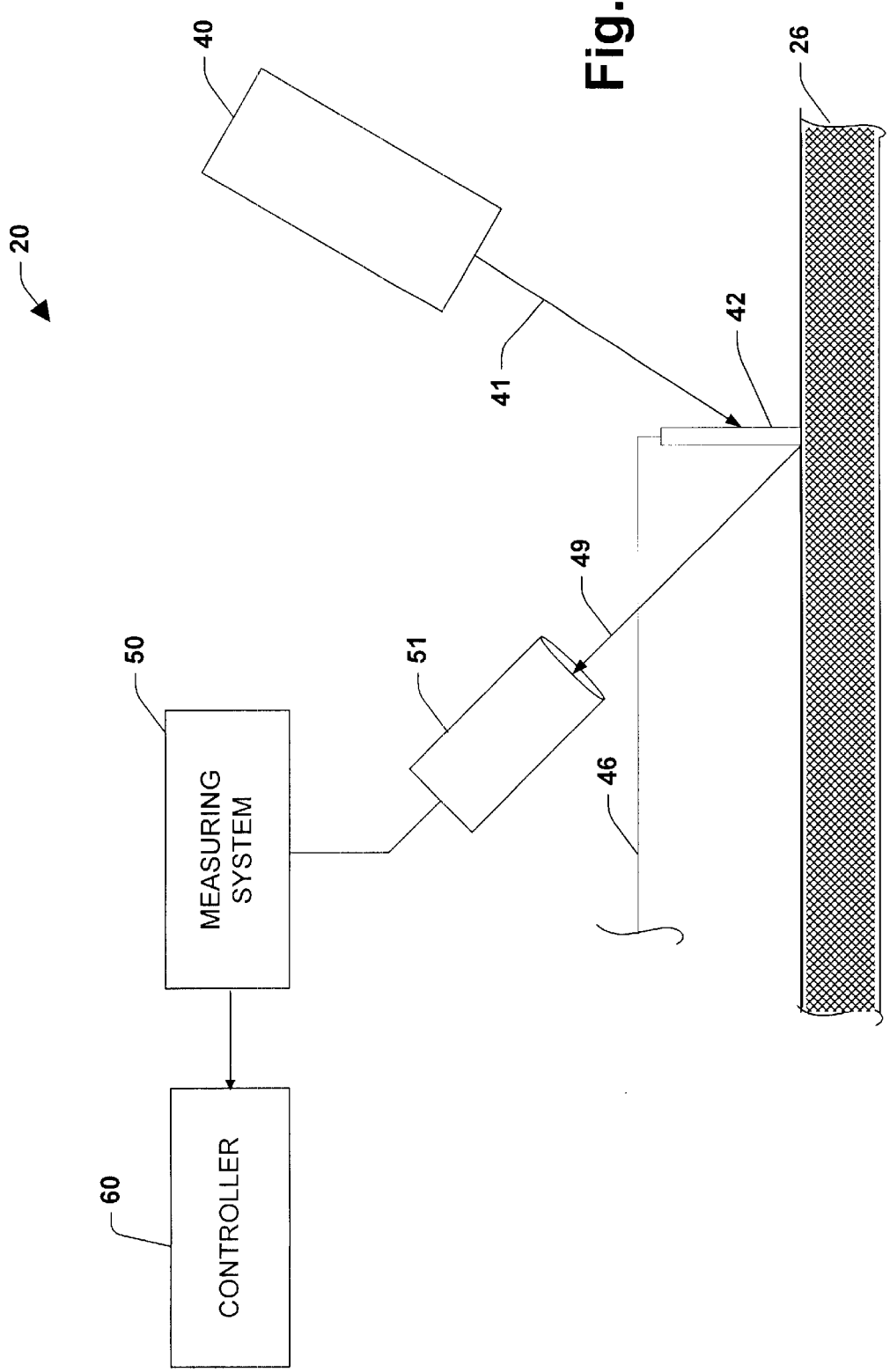
FIG. 1c is a partial schematic block diagram of the system of FIG. 1a being employed in connection with detecting a film/substrate composition or defect associated therewith by measuring the fluorescence from the tip of the scanning probe microscope in accordance with the present invention.

The present invention will now be described with reference to the drawings, wherein like reference numerals are used to refer to like elements throughout. The present invention generally relates to a system and method of detecting a film or substrate composition or of detecting a defect in a film or substrate using a scanning probe microscope. The scanning probe microscope utilizes a nanotube tip having material encapsulated therein or formed thereon which exhibits a detectable characteristic which varies as a function of the film/substrate composition therebeneath. That is, the detectable characteristic provides information regarding the composition of the film/substrate generally at the location wherein the nanotube tip resides. Preferably, the material is a fluorophore and the detectable characteristic is a fluorescence which is a function of the film/substrate composition (or defect thereat). By detecting the fluorescence (either the intensity or the wavelength) at the tip, the film/substrate composition can be readily ascertained at that location. By scanning the nanotube about the film/substrate surface, a composition and/or defect profile can be readily ascertained.

Referring initially to FIG. 1a, a film composition and/or defect detection system 20 is shown. The system 20 includes a substrate or film 26 for analysis. An excitation source 40, for example, a light excitation source such as a laser, is included in the system 20 and operates to transmit a focused beam of radiation 41 onto a tip 42 of a scanning probe microscope 44. The tip 42 is in contact with the film/substrate 26 via a cantilever beam 46 associated with the scanning probe microscope 44.

The tip 42 of the scanning probe microscope 44 includes a nanotube. Preferably, the nanotube is composed of carbon, however metallic or semiconductor type nanotubes may be utilized and are contemplated as falling within the scope of the present invention. According to a preferred embodiment of the present invention, the carbon nanotube is composed of one or more generally coaxial monoatomic sheets which are cylindrically wrapped about a center axis and have a generally cylindrical type hollow or space defined therein. Such an exemplary carbon nanotube is illustrated in FIG. 1b and is designated by reference numeral 48. The carbon nanotube 48 is an extremely slender carbon fibril, having a diameter that is typically measured in nanometers. For example, an exemplary nanotube 48 has a diameter of about 5–50 nanometers or less, however, other size nanotubes may be utilized and are contemplated as falling within the scope of the present invention.

The carbon nanotube 48 may be fabricated according to any one of a variety of different techniques. For example, the nanotube 48 may be synthesized using an arc-discharge method, wherein a plasma is generated between two graphite electrodes in a vacuum chamber filled with helium. Alternatively, the carbon nanotube 48 may be fabricated via laser ablation, wherein a graphite target mixed with metal catalysts are ablated at high temperature. In yet another alternative technique, the carbon nanotube 48 may be formed using chemical vapor deposition (CVD). Any manner of forming or otherwise growing the nanotube 48 may be utilized and is contemplated as falling within the scope of the present invention.

According to the present invention, the nanotube 48 has a material encapsulated therein or formed thereon which exhibits a characteristic which is detectable and which varies as a function of the film/substrate composition at the nanotube tip location. Therefore the characteristic can be monitored and used to determine the composition of the film/substrate 26 or whether a defect resides thereon or therein at the nanotube tip location. According to a preferred embodiment of the present invention, the material is a fluorophore.

A fluorophore is a substance which possesses a unique quality of producing light in response to being irradiated. Fluorophores therefore produce light after being excited by radiant energy, and the produced light generally is referred to as fluorescence. Fluorescence occurs when electrons, which have been displaced to excited states by energy absorbed during the irradiation, return to lower energy levels. Energy in the form of electromagnetic quanta is given off when the electrons return to the lower energy levels. Fluorescence begins when the fluorophore is irradiated and ends when irradiation ceases, with a relative short time delay, typically about 0.1–10 nsec. This extremely fast response time allows for monitoring and dynamic analysis of the film/substrate composition in substantially real time as the tip 42 scans across the film/substrate surface.

According to the present invention, the fluorophore is a composition sensitive fluorophore, which means that the degree to which fluorescence occurs (i.e., the magnitude and/or wavelength) is a function of the composition thereat. Various types of fluorophores may be utilized and are contemplated as falling within the scope of the present invention. For example, some composition sensitive fluorophores exhibit a variation in fluorescence intensity depending on the composition thereat while other types of fluorophores (e.g., europium chelates) exhibit a shift in fluorescence wavelength over variations in composition. This latter type of fluorophore is preferred because detecting a shift in radiation wavelength (i.e., color) is often easier than detecting a variation in fluorescence intensity since intensity measurements may require various component calibrations, etc. to know the incident calibration intensity, etc. However, any type of composition sensitive material may be utilized.

While not being bound or otherwise limited by an particular mechanistic explanation, a theoretical framework for the material excitation and related fluorescence based on the composition at the nanotube tip is provided below. Photochemical reactions generally occur when a particular type of compound absorbs light emitted by a radiation source. Of course, for the light radiation to be absorbed, the compound molecule must have an electronic transition between orbitals corresponding in energy to the emitted light. When a quantum of light is absorbed, the molecule is promoted to an excited electronic state. Once the excited state has been formed, the stage is set for a photochemical reaction. Not every molecule that is excited, however, will undergo a photochemical reaction because of the reactant (i.e., the film composition at the tip of the nanotube) in contact therewith. The degree to which molecules undergo a photochemical reaction is often called the quantum yield.

There are several believed reasons why some molecules in an excited state do not engage in a photochemical reaction. For example, some excited states are quenched, that is, a photoexcited state is deactivated by transferring its energy to another molecule (e.g., the composition at the nanotube tip). Because different compositions provide quenching of excited states to different degrees based on their atomic structure, etc., each composition under analysis provides a different quantum yield, which directly impacts the subsequent fluorescence. Those molecules which do not undergo a photochemical reaction have their electrons return to their initial energy levels, wherein the excited state returns to its ground state by the emission of light, which is often called a radiative transmission. This emission is the fluorescence of the material in the nanotube. Therefore it is believed that different compositions under analysis at the tip of the nanotube will impact uniquely the quantum yield of photochemical reactions by the fluorophores (and thus their fluorescence) and such information may be used to identify the composition type of a composition or identify a defect in such composition.

The system 20 utilizes the excitation source 40 such as a laser light source to focus a beam of radiation 41 on the tip 42. The excitation light or radiation 41 triggers a fluorescence 49 from the tip 42 (composed of the nanotube 48) as described above, a magnitude or wavelength of which is a function of the film/substrate 26 composition. The fluorescence 49 is detected and processed by a detection and measuring system 50 which measures the magnitude and/or wavelength of the fluorescence 49. Preferably, the measuring system 50 includes one or more photodetectors and/or spectrometers, however, any mechanism or sensor which is operable to detect a change in the material associated with the nanotube 48 as a function of substrate/film composition may be used and is contemplated as falling within the scope of the present invention. Photodetectors, spectrometers and various other detection systems are well known in the art, and therefore further discussion related thereto is omitted for the sake of brevity.

The material such as a fluorophore may be encapsulated within the nanotube 48 or affixed to an outside surface of the nanotube 48 in any one of a variety of methods. For example, a top portion of the nanotube 48 (which is normally closed) may be opened by subjecting the nanotube 48 to a selective reaction with the foreign material (e.g., a fluorophore) in a melted state under predetermined conditions, thereby breaking the top portion of the nanotube. Alternatively, the material may be introduced into the nanotube 48 in its gaseous phase. In yet another alternative method, the nanotube 48 may be exposed to a reactive gas or liquid to be selectively etched or be subjected to a high voltage such that the corona discharge breaks the top portion of the nanotube 48 to form an opening therein.

The introduction of the material (e.g., fluorophore) into the nanotube 48 may be accomplished either simultaneously with or after the formation of the opening in the nanotube 48. The introduction of the material into the nanotube 48 may be implemented by an evaporation of the material onto the nanotube and a subsequent heat treatment. Alternatively, the introduction can be implemented by contacting the open top of the nanotube 48 with a gaseous compound including the material or may be introduced into the nanotube 48 by capillary action with the material in liquid form. After the material is introduced into the nanotube 48, the opening on the top portion thereof is closed according to any one of several conventional techniques.

Alternatively, the material may be formed on an outside surface of the nanotube 48. For example, the outside surface of the nanotube 48 may be reacted or contacted with one or more substances to provide active sites for chemical substitution or physical absorption of different chemical species of interest. For example, the outside surface of the nanotube 48 may be oxidized, preferably non-uniformly, to support substitution with or reaction with the material such as a fluorophore. Any manner of coating the nanotube 48 with the material may be utilized and is contemplated as falling within the scope of the present invention.

In any event, the fluorescence 49 at the tip 42 is believed to be a function of the film/substrate composition local to the tip 42. Therefore, for example, if the tip 42 is scanning a polysilicon film, the fluorescence 49 at the tip 42 will be a function of the composition of the polysilicon (e.g., F(poly, $X_i, Y_j$)=$F_1$). If the tip 42 scans over a defect, the composition of the film at that point has changed, and therefore the fluorescence 49 at that point will change (e.g., F(poly, $X_m, Y_n$) =$F_2$). Therefore the fluorescence 49 carries information regarding the film composition that can be used to detect either a defect in the film/substrate 26 or other form of nonuniformity in the film composition.

According to another embodiment of the present invention, the fluorescence can be used to identify the composition of an unknown film. For example, since the fluorescence at the tip 42 is a function of the composition thereat, the fluorescence may be used to identify an unknown composition as well as its uniformity. Preferably, however, the system 20 of the present invention is used for identifying defects in the film/substrate 26. Since the fluorescence 49 includes identification information because the fluorescence 49 is a function of the composition at the tip 42, not only can film defects be detected, but the composition of the defect also may theoretically be established.

In the above exemplary embodiments of the present invention, a fluorophore which is excited by light radiation is employed. Alternatively, the material used in association with the tip 42 may be a material which exhibits chemiluminescence, electroluminescence or electrochemiluminescence, as may be desired. For example, such materials entail the creation of luminescent species by the chemical, electrical or electrochemical transfer of energy thereto (e.g., application of a voltage as the excitation source 40). Any method of excitation of the nanotube encapsulant or outside film may be utilized and is contemplated as falling within the scope of the present invention.

In addition, although the present invention has been discussed in conjunction with a hardened type film, the present invention is also applicable to the analysis of viscous fluids or unhardened films, for example, a pre-baked deposited photoresist film on a wafer. Therefore it is contemplated that the present invention extends to the analysis and detection of defects in a multitude of substances in various states.

A controller or processor 60 receives the measured data from the measuring system 50 and determines the film/substrate composition based on the detected fluorescence intensity magnitude or wavelength. In addition, the controller 60 is operatively coupled to the detection and measuring system 50 and is programmed to control and operate the various components within the system 20 in order to carry out the various functions described herein. The controller or processor 60 may be any of a plurality of processors, such as the AMD Athlon, K6 or other type architecture processors. The manner in which the controller 60 can be programmed to carry out the functions relating to the present invention will be readily apparent to those having ordinary skill in the art based on the description provided herein.

A memory 70 is also included in the system 20. The memory 70 is operatively coupled to the processor 60 and serves to store program code executed by the processor 60 for carrying out operating functions of the system 20 as described herein. The memory 70 includes, for example, read only memory (ROM) and random access memory (RAM). The ROM contains, among other code, the Basic Input-Output System (BIOS) which controls the basic hardware operations of the system 20. The RAM preferably is the main memory into which the operating system and application programs are loaded. The memory 70 also serves as a storage medium for temporarily storing information such as the detected fluorescence magnitude and/or wavelength (or other type detectable characteristic), fluorescence tables, film/substrate coordinate tables, fluorescence information, scanning probe microscope information, and other data which may be employed in carrying out the present invention. For mass data storage, the memory 70 may include a hard disk drive (e.g., a 10 Gigabyte hard drive).

A power supply 78 provides operating power to the system 20. Any suitable power supply (e.g., battery, line power) may be employed to carry out the present invention.

The processor 60 is also coupled to the scanning probe microscope 44 which operates the scanning of the tip 42 across the film/substrate 26. According to preferred embodiments of the present invention, the scanning probe microscope 44 may be either a scanning tunneling microscope (STM), a scanning force microscope (SFM), or an atomic force microscope (AFM), as may be desired. As is generally well known to those skilled in the art, an STM uses a field emission of electrons from the electrode tip 42. The STM is often used as a maskless lithography tool to expose a resist. The electrons from the electrode tip 42 pass through the resist down to the substrate to thereby expose the resist. In contrast, SFMs and AFMs are both often used to map or image a surface topography of a sample by scanning the tip 42 over the sample 26. The tip position is controlled by maintaining a constant force of the tip 42 on the sample 26, and the deflection of the cantilever 46 to which the tip 42 is attached is monitored to map the surface topography of the sample. By employing such scanning probe tools utilizing the nanotube tip 48 of the present invention as the scanning tip 42, a defect profile or film composition profile may be readily ascertained across the surface of the film/substrate 26.

The system 20 is operable to detect a defect profile or determine a film/substrate composition in the following exemplary fashion, as will be described in conjunction with FIGS. 1c–4. According to this example, the tip 42 employing the nanotube 48 is scanned across the film/substrate in a predetermined manner, as dictated by the controller 60. Accordingly, the film/substrate 26 preferably is mapped by the controller 60 into a grid 100 as illustrated in FIG. 2, wherein each portion of grid 100 corresponds to an XY position. Depending on the desired system resolution, the number of XY locations on the grid 100 may vary as desired.

When the controller 60 determines that the tip 42 is at location $(X_i, Y_j)$, the controller also controls the light source 40 to focus light 41 onto the tip 42 to excite the material associated therewith, as illustrated in FIG. 1c. The light source 40 (e.g., the laser) then irradiates the tip 42 to produce light 49 (fluorescence), having a magnitude or wavelength which is a function of the film/substrate composition thereat $F(X_i, Y_j)$. The fluorescence 49 is detected by, for example, a photodetector or spectrometer 51 associated with the measuring system 50 and converted into data, for example, analog signals which represent the fluorescence magnitudes or wavelengths at the various locations. Preferably, the analog signals are converted into digital data using, for example, an analog to digital (A/D) converter, which are then transmitted to the controller 60 for further processing. The controller 60 analyzes the fluorescence magnitude or wavelength data according to its programming to generate, for example, a fluorescence profile across a plurality of locations $(F(X_i, Y_j)...F(X_m, Y_n))$ on the film/substrate 26 as the tip 42 is scanned across the film/substrate surface, as illustrated in FIG. 3.

Upon identifying the fluorescence at various locations, the controller 60 then may perform various types of analysis depending on its programming and desired function. For example, if one is attempting to identify a defect profile across the film 26, the controller 60 preferably compares the fluorescence at each location to one or more predetermined fluorescence thresholds. For example, if the fluorescence at a location $(X_i, Y_j)$ is greater than a lower threshold $F_L$ and less than an upper threshold $F_H$, then the fluorescence at that location is within an acceptable range for the film being scanned and the controller 60 labels that location $(X_i, Y_j)$ as acceptable $(F_A)$, that is, no defect is present at that location. If, however, the fluorescence at the location falls below or exceeds the respective thresholds, the controller 60 identifies the fluorescence as too high or too low $(F_u)$. More particularly, the controller 60 identifies that a defect exists at the location (e.g., $X_6, Y_7$) associated with the fluorescence which fell outside the expected range for the film being evaluated. The controller 60 then stores such conclusion data in the memory 70 and/or transmits the data to the display 80 for user analysis, as may be desired. The controller 60 thereby generates a mapping as illustrated in FIG. 4 which indicates the status of the film/substrate composition across the film surface.

According to another alternative embodiment of the present invention, the system 20 may identify the existence of a defect as well as provide information regarding the defect type. For example, if a polysilicon film is being scanned by the scanning probe microscope 44 using the tip 42, and an aluminum particulate defect resides either on the top surface of the film or embedded therein, the fluorescence 49 from the tip 42 will have an intensity or wavelength that is a function of the aluminum composition. According to the present invention, the controller 60 is further configured to correlate the detected fluorescence to the appropriate composition type. In the same manner, the system 20 of the present invention may be used to identify an unknown film composition.

Figure 5:
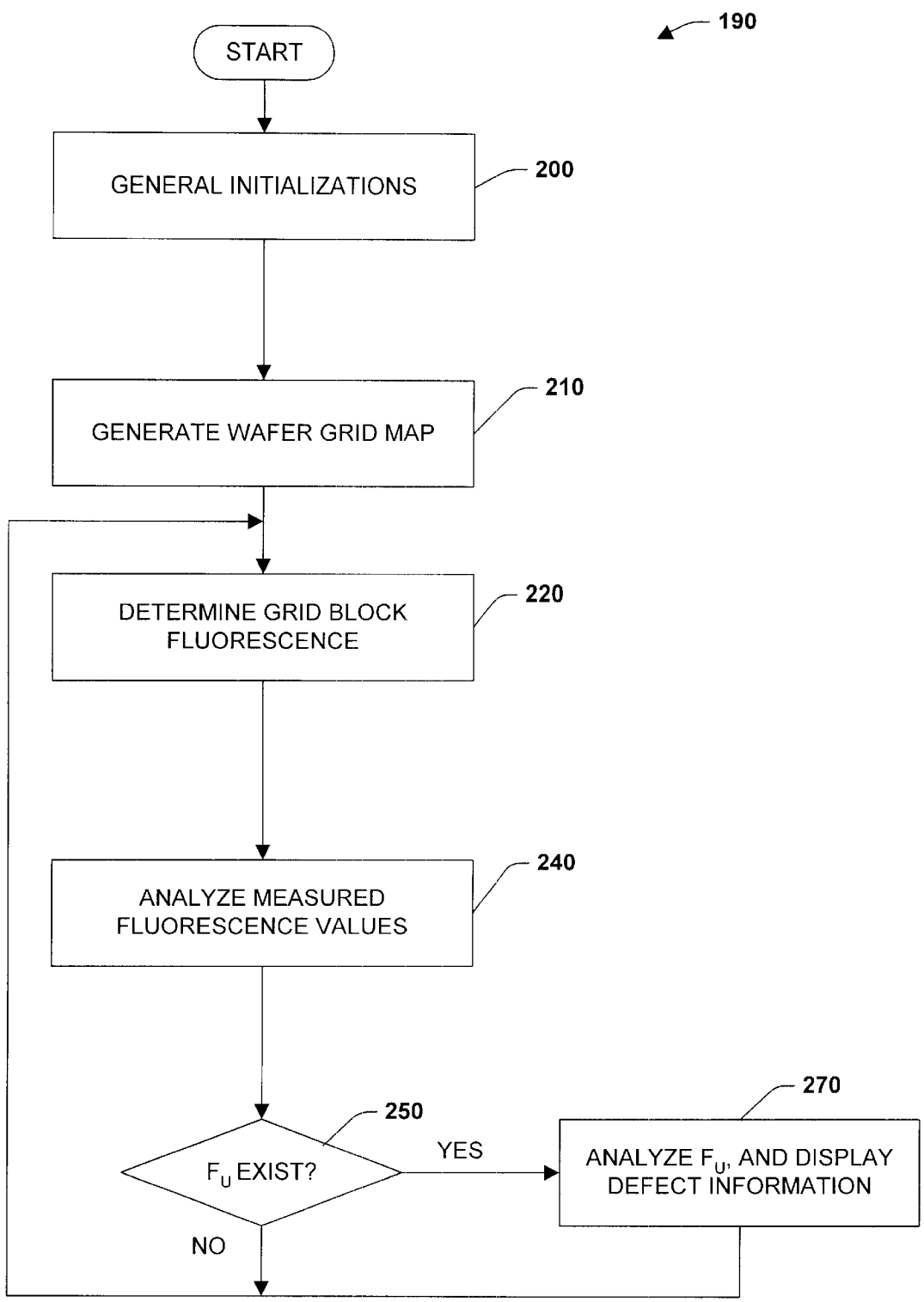
FIG. 5 is a flow chart diagram illustrating one exemplary methodology for carrying out the present invention.

FIG. 5 is a flow chart diagram illustrating one particular methodology 190 for carrying out the present invention. In step 200, the controller or processor 60 performs general initializations to the detection system 20. In step 210, the controller 60 maps at least a portion of the film/substrate 26 into a plurality of grid blocks "XY". In step 220, the tip 42 is scanned across the surface of the film/substrate 26 while light is focused on the tip 42 and characteristic such as fluorescence is detected and measured by the measurement system 50 and the controller 60 with respect to the various film/substrate portions mapped by the respective grid blocks XY. The controller 60 then analyzes the determined fluorescence values (e.g., intensity and/or wavelength) against a table of acceptable fluorescence levels or various predetermined fluorescence thresholds for the respective portions of the film/substrate 26. In step 250, the controller 60 determines if any grid block fluorescence values are not acceptable. If all values grid block fluorescence values are acceptable (NO at step 250), the controller 60 ends this particular iteration of the present methodology 190 and returns to step 220 to perform another iteration. If unacceptable fluorescence values are found for any of the grid blocks (YES), the controller 60 advances to step 270 where the data associated with the defect is stored in the memory 70 and/or transmitted to the display 80 for user analysis, for example, as illustrated in FIG. 6.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described components (assemblies, devices, circuits, etc.), the terms (including a reference to a "means") used to describe such components are intended to correspond, unless otherwise indicated, to any component which performs the specified function of the described component (i.e., that is functionally equivalent), even though not structurally equivalent to the disclosed structure which performs the function in the herein illustrated exemplary embodiments of the invention. In addition, while a particular feature of the invention may have been disclosed with respect to only one of several embodiments, such feature may be combined with one or more other features of the other embodiments as may be desired and advantageous for any given or particular application.

What is claimed is:

1. A system for analyzing a film and detecting a defect associated therewith, comprising:
    a scanning probe microscope including a nanotube tip having a material associated therewith which exhibits a characteristic that varies with respect to a film composition at a location corresponding to the nanotube tip, wherein the material comprises a fluorophore, and wherein the characteristic is a fluorescence having a wavelength that varies over variations in the film composition at the location corresponding to the nanotube tip;
    an excitation source for triggering the characteristic which varies with respect to the film composition at the location corresponding to the nanotube tip, wherein the excitation source comprises a light source;
    a detection system for detecting the material characteristic; and
    a controller operatively coupled to the detection system and the scanning probe microscope, the controller configured to receive information associated with the detected characteristic and use the information to determine whether the film contains a defect at the location corresponding to the nanotube tip.

2. The system of claim 1, wherein the material is in the nanotube.

3. The system of claim 1, wherein the material is on an outside surface of the nanotube.

4. The system of claim 1, wherein the detection system comprises:
    a detector which senses the material characteristic; and
    a measuring system operatively coupled to the detector, wherein the measuring system converts the detected material characteristic into a data form for processing by the controller.

5. The system of claim 4, wherein the measuring system comprises an analog to digital converter.

6. The system of claim 4, wherein the detector comprises a spectrometer.

7. The system of claim 4, wherein the detector comprises a photodetector.

8. The system of claim 1, further comprising a display operatively coupled to the controller, the display providing a visual indication of information relating to the defect determination.

9. The system of claim 1, wherein the scanning probe microscope is selected from the group consisting of a scanning tunneling microscope, a scanning force microscope and an atomic force microscope.

10. The system of claim 1, wherein the nanotube tip comprises a carbon nanotube.

11. A system for analyzing a film and detecting a defect associated therewith, comprising:
    a scanning probe microscope including a nanotube tip having a material associated therewith which exhibits a characteristic that varies with respect to a film composition at a location corresponding to the nanotube tip, wherein the material is an electroluminescent or electrochemiluminescent species, and wherein the characteristic is a fluorescence having an intensity or wavelength that varies over variations in the film composition at the location corresponding to the nanotube tip;
    an excitation source for triggering the characteristic which varies with respect to the film composition at the location corresponding to the nanotube tip, wherein the excitation source is a voltage;
    a detection system for detecting the material characteristic; and
    a controller operatively coupled to the detection system and the scanning probe microscope, the controller configured to receive information associated with the detected characteristic and use the information to determine whether the film contains a defect at the location corresponding to the nanotube tip.

12. A system for determining a film composition at a particular location of a film or substrate, comprising:
    a scanning probe microscope including a nanotube tip having a material associated therewith which exhibits a fluorescence upon excitation that varies with respect to a film composition at a location corresponding to the nanotube tip;
    an excitation source which directs radiation to the nanotube to excite the material associated therewith;
    a detection system for detecting the fluorescence from the nanotube tip; and
    a controller operatively coupled to the detection system, the excitation source and the scanning probe microscope, the controller configured to receive information associated with the detected fluorescence and use the information to determine whether the film contains a defect at the location corresponding to the nanotube tip.

13. The system of claim 12, wherein the controller is further configured to compare a fluorescence from the nanotube tip to a predetermined threshold and make the determination whether the film contains a defect at the location based on the comparison.

14. The system of claim 12, wherein the fluorescence comprises one of a fluorescence intensity and a fluorescence wavelength.

15. The system of claim 12, wherein the nanotube tip comprises a carbon nanotube.

16. The system of claim 12, wherein the scanning probe microscope comprises an atomic force microscope.

17. A method of detecting a film composition at a particular location of a film or substrate, comprising the steps of:
    associating a material exhibiting a characteristic which varies with respect to a film composition with a nanotube tip of a scanning probe microscope, wherein the material comprises a fluorophore;
    detecting the characteristic, wherein detecting the characteristic comprises:
        irradiating the nanotube tip having the fluorophore associated therewith; and
        sensing a fluorescence from the irradiated nanotube tip, wherein the fluorescence is a function of the film composition at a location corresponding to the nanotube tip, wherein sensing the fluorescence comprises sensing a wavelength of the fluorescence, wherein the wavelength is a function of the film composition; and determining a composition of a portion of the film using the detected characteristic.

18. The method of claim 17, wherein associating the material with the nanotube tip comprises encapsulating the material in the nanotube.

19. The method of claim 17, wherein associating the material with the nanotube tip comprises depositing the material on an outer surface of the nanotube.

20. The method of claim 17, wherein sensing the fluorescence comprises sensing an intensity of the fluorescence, wherein the intensity is a function of the film composition.

21. The method of claim 17, wherein determining the composition of a portion of the film comprises:

comparing the detected characteristic to a predetermined threshold; and determining whether the portion of the film contains a defect based on the comparison.

22. The method of claim 17, wherein determining the composition of a portion of the film comprises:

comparing the detected characteristic to another detected characteristic corresponding to another portion of the film; and determining whether the portion of the film contains a defect based on the comparison.

* * * * *

UNITED STATES PATENT AND TRADEMARK OFFICE
CERTIFICATE OF CORRECTION

PATENT NO.   : 6,437,329 B1
DATED        : August 20, 2002
INVENTOR(S)  : Sanjay J. Yedur, Bhanwar Singh and Bryan K. Choo It is certified that error appears in the above-identified patent and that said Letters Patent is hereby corrected as shown below:

Column 1,
Line 51, please replace the word "deceased" with the word -- decreased --.

Column 7,
Line 39, please replace the phrase "of grid" with -- of the grid --.

Signed and Sealed this

Thirty-first Day of December, 2002

JAMES E. ROGAN
*Director of the United States Patent and Trademark Office*